US00PP35675P2

(12) United States Plant Patent
Hansen

(10) Patent No.: US PP35,675 P2
(45) Date of Patent: Mar. 5, 2024

(54) **X *HEUCHERELLA* PLANT NAMED 'CAPTURE THE FLAG'**

(50) Latin Name: **x *Heucherella* (*Heuchera* times *Tiarella*)**
Varietal Denomination: Capture the Flag

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,350

(22) Filed: Jul. 25, 2023

(51) Int. Cl.
*A01H 5/02* (2018.01)
*A01H 6/80* (2018.01)

(52) U.S. Cl.
USPC ..... Plt./441

(58) Field of Classification Search
USPC ..... Plt./263.1, 441
See application file for complete search history.

*Primary Examiner* — Karen M Redden

(57) ABSTRACT

The new hybrid x *Heucherella* plant named 'Capture the Flag' with large palmately-lobed leaves that are, moderately to deeply dissected into five to seven main lobes with each individual lobes incised to about two-thirds of the way to the main vein. Foliage color starts in the spring as chartreuse, becoming more yellowish, with reddish-burgundy surrounding the veins and toward margins in narrow lines. 'Capture the Flag' is vigorous and produces numerous sterile creamy-white flowers in narrow densely-branched panicles beginning in late spring and exhibits good heat and humidity tolerance. The plant is useful for landscaping as a specimen color, en masse, or as a container plant.

2 Drawing Sheets

Botanical denomination: x *Heucherella* (*Heuchera* times *Tiarella*).

Cultivar designation: 'Capture the Flag'.

STATEMENT REGARDING PRIOR DISCLOSURES UNDER 37 CFR 1.77(B)(6)

The first offer for sale of the new plant anywhere in the world was on Aug. 15, 2022, by Walters Gardens, Inc. The first description of the new plant was on a website operated by Walters Gardens, Inc. on Feb. 1, 2023. This was followed by a small photograph and brief description in the "Walters Gardens 2023-2024 Catalog" first distributed on May 19, 2023. Walters Gardens, Inc. obtained the new plant and all information about the new plant from the inventor. No plants of x *Heucherella* 'Capture the Flag' have been sold in this country or anywhere in the world, nor has any disclosure of the new plant been made, more than one year prior to the filing date of this application, and such sale or disclosure within one year was either derived directly or indirectly from the inventor and thus should be considered a 35 U.S.C. § 102(b) exception.

BACKGROUND OF THE INVENTION

The present invention relates to a new and distinct intergeneric hybrid between Coral Bells and Foam Flower, both in the Saxifragaceae family and given the cultivar name of 'Capture the Flag' with the combined generic epithet x *Heucherella*. x *Heucherella* 'Capture the Flag' resulted from an intentional cross between *Heuchera* 'Red Lightning' U.S. Plant Pat. No. 27,767 as the female or seed parent and the unreleased, proprietary hybrid known as *Tiarella* 15-1-29 (not patented) as the male or pollen parent. The cross was hybridized by the inventor at a wholesale perennial nursery in Zeeland, Michigan, USA on Jan. 24, 2017. The new plant was selected from among many other crosses and x *Heucherella* seedlings growing at the same nursery which met the rigorous criteria of excellent foliage, vigor, and habit and was assigned the breeder code of 18-54-1.

x *Heucherella* 'Capture the Flag' has been asexually propagated initially by basal cuttings in 2019 at a nursery in Zeeland, Michigan, and since by sterile tissue culture propagation. The resultant asexually propagated plants have remained stable and exhibit the same characteristics as the original plant over multiple generations.

BRIEF SUMMARY OF THE INVENTION x *Heucherella* 'Capture the Flag' differs from its parents as well as all other X *Heucherella* known to the applicant. The most similar cultivars are: x *Heucherella* 'Eye Spy' U.S. Plant Pat. No. 21,296, 'Catching Fire' U.S. Plant Pat. No. 31,065, and 'Stoplight' U.S. Plant Pat. No. 16,835.

Compared with the female parent, *Heuchera* 'Red Lightning', the new plant has a smaller habit, smaller leaves, shorter panicles, has more acute, and deeper dissected leaf lobes. The male parent, *Tiarella* 15-1-29, has more dissected and narrower leaf lobes and the foliage color is medium green.

'Eye Spy' has narrower and more dissected leaf lobes and more and denser panicles of pinkish flowers. 'Catching Fire' has leaves that have shorter lobes with more rounded apices, and the center mahogany markings are thicker with fewer narrow branches along the veins. 'Stoplight' has foliage that has less divided lobes with thicker burgundy center markings.

The new plant differs from all *Heuchera*, x *Heucherella*, and *Tiarella* known to the inventor in the following combined traits:

1. The large foliage that is chartreuse with reddish-burgundy centers surrounding the veins and extending toward margins in narrow lines;
2. Leaves have narrow moderately to deeply dissected lobes;
3. The flowers are creamy-white;
4. Habit develops into a large mound with multiple tightly clustered shoots emerging at the base;
5. The plant is more robust, and more heat tolerant than typical x *Heucherella*.

BRIEF DESCRIPTION OF THE DRAWING

The photographs of the new plant demonstrate the overall appearance of the plant including the unique traits. The plant in the photograph is a two-year-old plant grown at a wholesale perennial nursery in Zeeland, Michigan, USA. The colors are as accurate as reasonably possible with color reproductions. Some slight variations of color may occur as a result of lighting quality, intensity, wavelength, and direction or reflection.

DETAILED BOTANICAL DESCRIPTION

Figure 1:
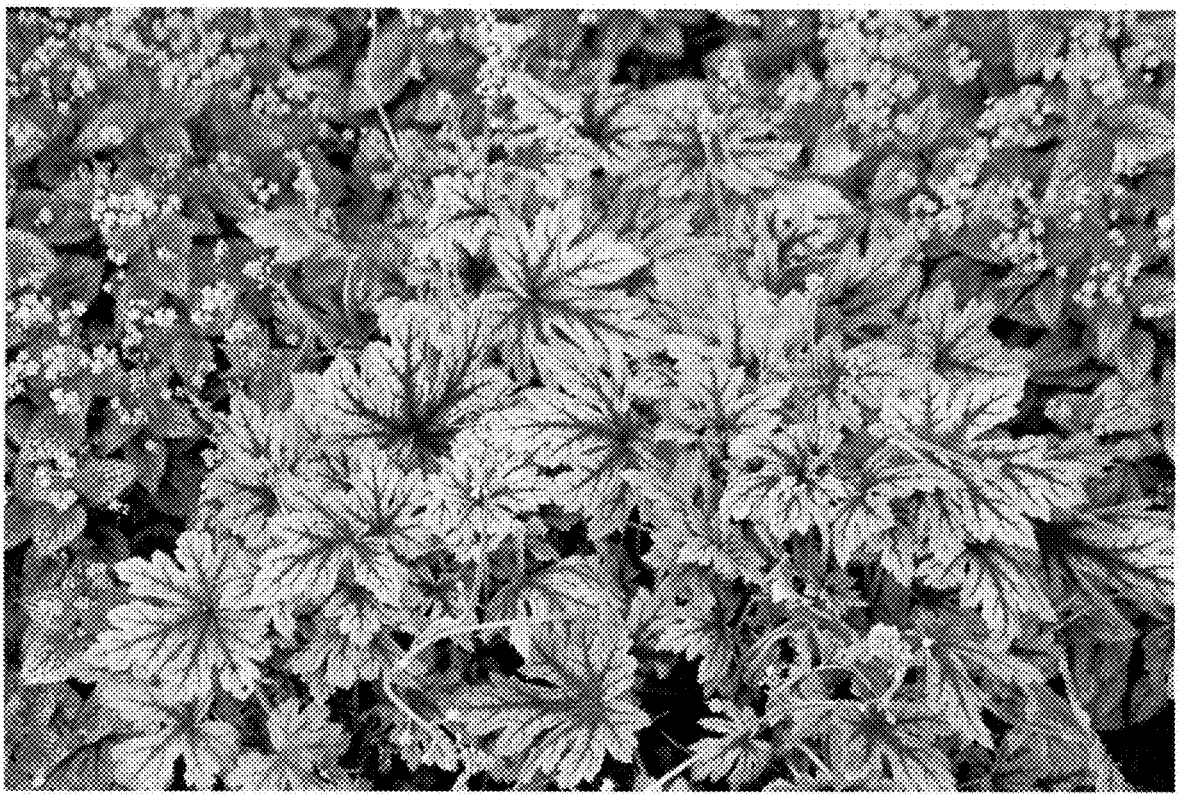
FIG. 1 shows the new plant in late spring.
Figure 2:
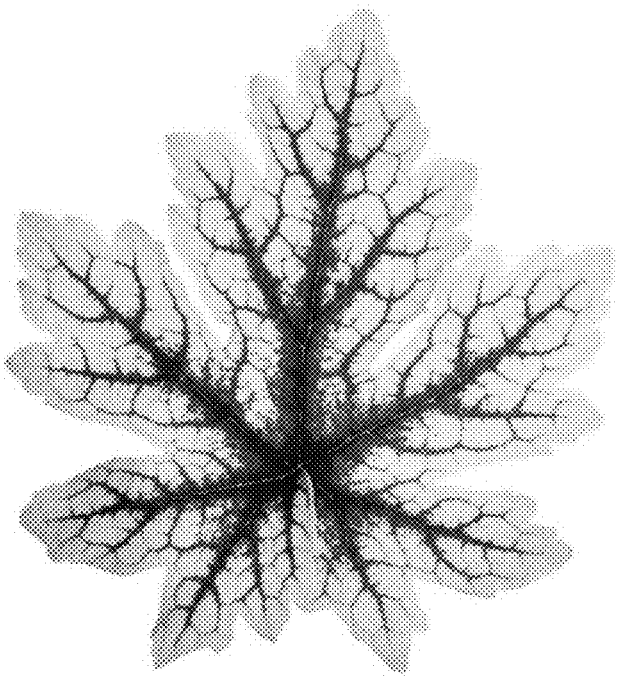
FIG. 2 shows a close-up of the foliage in mid-summer.
Figure 3:
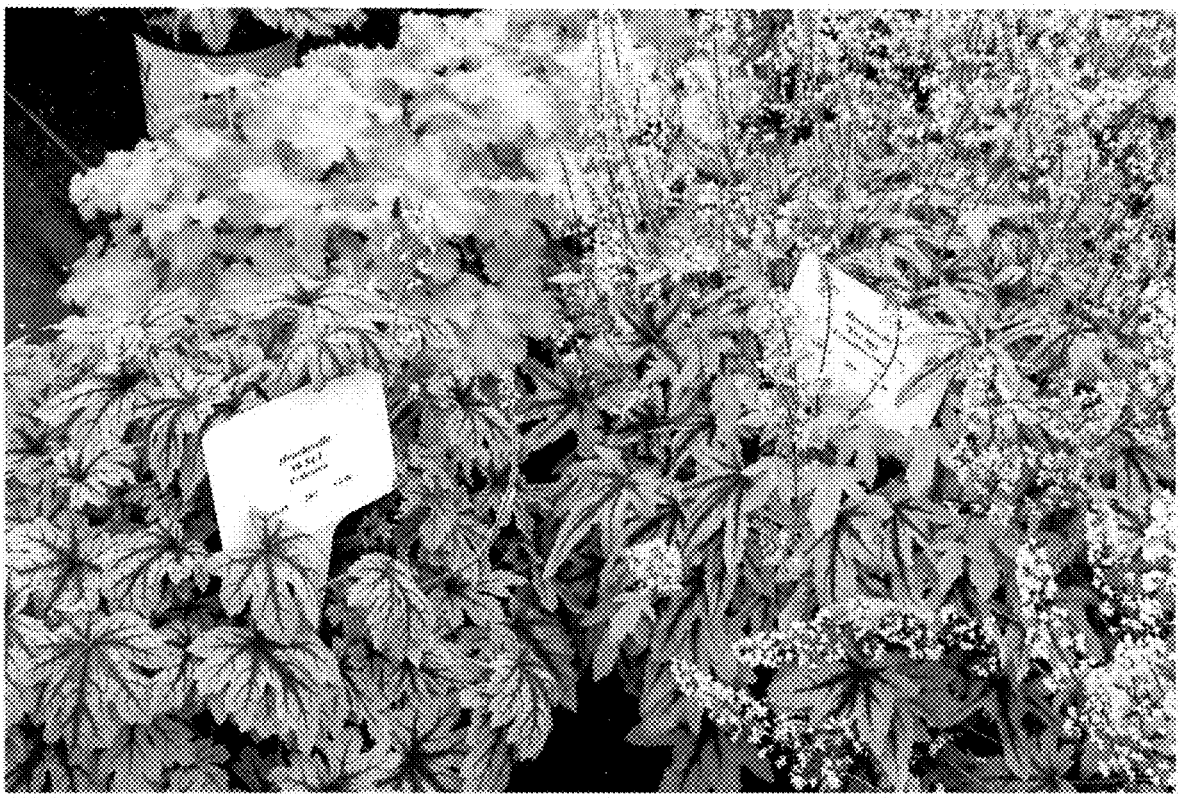
FIG. 3 shows a comparison between 'Capture the Flag' (left) and 'Eye Spy' (right).

The following description is based on two-year-old plants growing in a partially shaded greenhouse with supplemental water and fertilizer at a wholesale perennial nursery in Zeeland, Michigan, USA. 'Capture the Flag' has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

Parentage: The female or seed parent is *Heuchera* 'Red Lighting'; the male or pollen parent was *Tiarella* 15-1-29;

Plant habit: Hardy herbaceous perennial of tightly compact rhizomes with basal rosette in a rounded mound of foliage; foliage about 25 cm tall and 60 cm across;

Roots: Fibrous, finely branched; when actively growing near white in color depending on soil type, nearest RHS 158D;

Growth rate: Rapid, rooting from cutting in 2 weeks and finishing in a three-liter container in about 3 months;

Foliage: Palmately lobed into five to seven irregular main lobes; pubescent adaxial and abaxial; lobes moderately to deeply dissected to about two-thirds of the way to petiole; secondary lobes are dissected to nearly halfway to primary veins; matte surface above and below; main and secondary lobes with acute apices; margins ciliolate and distally serrate; cordate base with lobes imbricate about 1 cm; cauline leaves on up to first two nodes below flowers and decreasing in size distally; foliage density dense;

Foliage size: Blade to about 15 cm long and 15 cm wide, average about 9.5 cm long and 9 cm wide; center lobe about 8 cm long and about 6.5 cm wide; cauline leaves to 5 cm long and 5 cm wide;

Foliage margin indentations: Moderately to deeply dissected;

Foliage color: Seasonally variable; spring and young emerging leaves adaxial nearest RHS 145A toward margin portions and the center inner palm surrounding the main veins nearest RHS 187B; abaxial spring emerging leaves nearest RHS 145A near margins and surrounding veins nearest RHS 187A; when first flowering adaxial margin portion between RHS 9A and RHS 11A, and center portion surrounding the veins nearest RHS 187B; when first flowering abaxial between RHS 145A and RHS 11A in margin portions and surrounding veins nearest RHS 187A; late summer and fall adaxial area surrounding veins variable, between RHS 146C and RHS 147C, between RHS 146B and RHS 147B, with a faint silver overlay of nearest RHS 192A showing on some leaves, area surrounding veins nearest RHS Ni 87A; late summer and fall abaxial margin portions variable, nearest RHS 146D and between RHS 138A and RHS 138B, portion surrounding the veins with undertone of nearest RHS N187A;

Leaf margin: Serrate and ciliolate;

Leaf apex: Acute;

Leaf base: Cordate with lobes sometimes imbricate by about 1 cm;

Leaf surface: Slightly cupped at petiole; flat margins; pubescent adaxial and abaxial;

Leaf quantity: About six per division and 60 per plant;

Veins: Palmate, puberulent adaxial, pubescent abaxial;

Vein color: Adaxial early season main veins nearest RHS 145A and secondary veins nearest RHS 146C, abaxial early season main veins between RHS 145C and RHS 148D, secondary veins nearest RHS 145A; flowering season adaxial main veins nearest RHS 146D and secondary veins nearest RHS 143A, flowering season abaxial main veins between RHS 146D and RHS 145C, secondary veins nearest 146D; late summer and fall season adaxial main veins nearest RHS 146D, and distally between RHS 143A and RHS 144A; late summer and fall season abaxial main veins between RHS 146D and RHS 145C, secondary veins nearest 146B;

Petiole: Cylindrical, hirsutulous, to about 26 cm long and 3 mm diameter above stipule; wiry but flexible;

Petiole color: On emerging foliage proximally nearest RHS 183C and in the distal 3 cm between RHS 146D and RHS 145C; mid-flowering season nearest RHS 146D with a blush proximally of nearest RHS 183C, and late summer and fall blend nearest RHS 146D;

Inflorescence: In open narrowly-branched panicle, to about 10 panicles per plant; to about 150 flowers per panicle; first panicle flowering beginning late May in Michigan and remaining in flower for about three weeks; repeat panicles until early fall; individual flowers remaining open about three to four days; plant remains in flower with new panicles for about ten weeks;

Branches: To about 43; cylindrical; puberulent; ascending; proximal branches to about 8 cm long and 1 mm diameter at base; color nearest RHS 146D;

Fragrance: None detected;

Peduncle: Cylindrical; hirsutulous to pubescent with hairs to about 2 mm long; to about 62 cm tall and 3 mm diameter at base, flowering portion about 30 cm tall and 4.5 cm wide; with cauline leaves at lower two to four nodes; mostly upright with random bends; flower density medium;

Peduncle color: Nearest RHS 146D;

Peduncle branches: To about 47 per panicle; short and moderately-densely flowered; lowest branches with about 6 flowers; to about 2.5 cm long and 1 mm diameter; decreasing in size and flower quantity per branch distally;

Cauline leaves: Palmate; to about 5.5 cm long and 5.5 cm wide; with petioles about 3.5 cm long and 1 mm diameter at base, decreasing distally; color of cauline leaves and petioles same as other foliage;

Pedicel: Cylindrical; glandular to puberulent; about 2 mm long and 0.5 mm diameter;

Pedicel color: Nearest RHS 195A;

Buds one day prior to opening: Oblong elliptical; about 3 mm long and 2 mm diameter;

Bud color: Distal one-third between RHS 157A and RHS 144D, proximal portion nearest RHS NN155A;

Flower: Perfect; campanulate; about 5 mm deep and 9 mm in diameter at face; individual flowers lasting about four to five days on plant or as cut flower; attitude outwards to slightly drooping;

Calyx: Five sepals; about 6 mm across and 3 mm deep; fused in basal 2 mm into hypanthium;

Sepals: Glabrous adaxial, glandular abaxial; apex acute, margin entire; to about 3.5 mm long and 1.5 mm wide;

Calyx color: Adaxial and abaxial nearest RHS NN155D with the adaxial and abaxial apical 0.5 mm between RHS 157A and RHS 144D;

Petals: Typically, five; spatulate, narrowly acute apex, narrowly attenuate base; margin entire; glabrous abaxial and adaxial; about 5.5 mm long and 0.8 mm wide;

Petal color: Abaxial nearest RHS NN155C; adaxial nearest RHS NN155C;

Androecium:

*Filaments*.—Typically, ten, thin, about 5 mm long and less than 0.3 mm in diameter; color nearest RHS NN155C.

*Anthers*.—Vestigial; oblong to nearly 0.7 mm long and about 0.4 mm wide; color nearest RHS N25A.

*Pollen*.—Not observed.

Gynoecium:

*Pistil*.—One central two-beaked pistil, about 5 mm long.

*Stigma*.—Minute, about 0.2 mm diameter; color nearest RHS NN155C to transparent.

*Ovary*.—Two carpels; apex tapering to meet pistil; rounded base and sides; to about 1.5 mm diameter at base and about 1 mm tall; color nearest RHS NN155B.

*Style*.—About 4 mm long; narrowing to 0.1 mm at stigma; color nearest RHS NN155C.

Fruit: two-beaked capsule, about 4 mm long and 2 mm in diameter at widest portion; color nearest RHS 200A when mature;

Seed: Not observed;

Growth conditions: X *Heucherella* 'Capture the Flag' grows best with ample moisture and drainage in either filtered or part sun. Cold hardy from USDA zones 4 to 9, 'Capture the Flag' is able to tolerate heat and humidity better than many x *Heucherella*.

Disease and pest tolerance: Other pest and disease resistance and tolerance outside of that normal for x *Heucherella* is not known. The new plant may be susceptible to diseases and pests common to other x *Heucherella*.

It is claimed:

1. The new and distinct ornamental x *Heucherella* plant named 'Capture the Flag' as herein described and illustrated.

* * * * *